(12) United States Patent
Hestad et al.

(10) Patent No.: US 8,460,300 B2
(45) Date of Patent: Jun. 11, 2013

(54) INSTRUMENTATION AND ASSOCIATED TECHNIQUES FOR MINIMALLY INVASIVE VERTEBRAL ROD INSTALLATION

(75) Inventors: Hugh D. Hestad, Edina, MN (US); W. Matthew Kuester, St. Louis Park, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1245 days.

(21) Appl. No.: 11/761,387

(22) Filed: Jun. 12, 2007

(65) Prior Publication Data
US 2008/0312703 A1    Dec. 18, 2008

(51) Int. Cl.
*A61B 17/70*    (2006.01)

(52) U.S. Cl.
USPC ........................................ 606/86 A; 606/86 R

(58) Field of Classification Search
CPC ............. A61B 17/7083; A61B 17/7086; A61B 17/7088; A61B 17/7089
USPC ........................ 606/86 A, 86 B, 86 R, 99, 100
See application file for complete search history.

(56) References Cited

U.S. PATENT DOCUMENTS

| | | | |
|---|---|---|---|
| 5,242,443 A | 9/1993 | Kambin | |
| 6,235,028 B1 | 5/2001 | Brumfield et al. | |
| 6,951,538 B2 | 10/2005 | Ritland | |
| 7,008,424 B2 | 3/2006 | Teitelbaum | |
| 7,250,052 B2 | 7/2007 | Landry et al. | |
| 2004/0039384 A1 | 2/2004 | Boehm, Jr. et al. | |
| 2004/0138662 A1 | 7/2004 | Landry et al. | |
| 2004/0143265 A1 | 7/2004 | Landry et al. | |
| 2004/0172022 A1 | 9/2004 | Landry et al. | |
| 2005/0021031 A1* | 1/2005 | Foley et al. | 606/61 |
| 2005/0065517 A1 | 3/2005 | Chin | |
| 2005/0131408 A1 | 6/2005 | Sicvol et al. | |
| 2005/0131421 A1 | 6/2005 | Anderson et al. | |
| 2005/0149053 A1* | 7/2005 | Varieur et al. | 606/104 |
| 2005/0192589 A1* | 9/2005 | Raymond et al. | 606/99 |
| 2005/0215999 A1 | 9/2005 | Birkmeyer et al. | |
| 2005/0228380 A1 | 10/2005 | Moore et al. | |
| 2005/0234449 A1 | 10/2005 | Aferzon | |
| 2006/0074418 A1* | 4/2006 | Jackson | 606/61 |
| 2006/0247630 A1* | 11/2006 | Iott et al. | 606/61 |

* cited by examiner

*Primary Examiner* — Eduardo C Robert
*Assistant Examiner* — Julianna N Harvey
(74) *Attorney, Agent, or Firm* — Seager, Tufte & Wickhem, LLC

(57) ABSTRACT

Spinal fixation systems may be installed utilizing instruments and techniques alone or in combination with selectively attached extension members mounted on vertebral anchors to extend percutaneously from the spine. The surgical procedures associated with this invention involve making small, discrete incisions for the placement of select vertebral anchors. The extension members retract soft tissue, muscle and the like to thereby provide visibility and access to the head of the anchor. Instrumentation is utilized to deliver and install components such as a spine rod, set screw and other required hardware to the anchors. Once a spine rod or other components are secured to the pedicle screws, the instrumentation and extension members are removed from the patient.

11 Claims, 15 Drawing Sheets

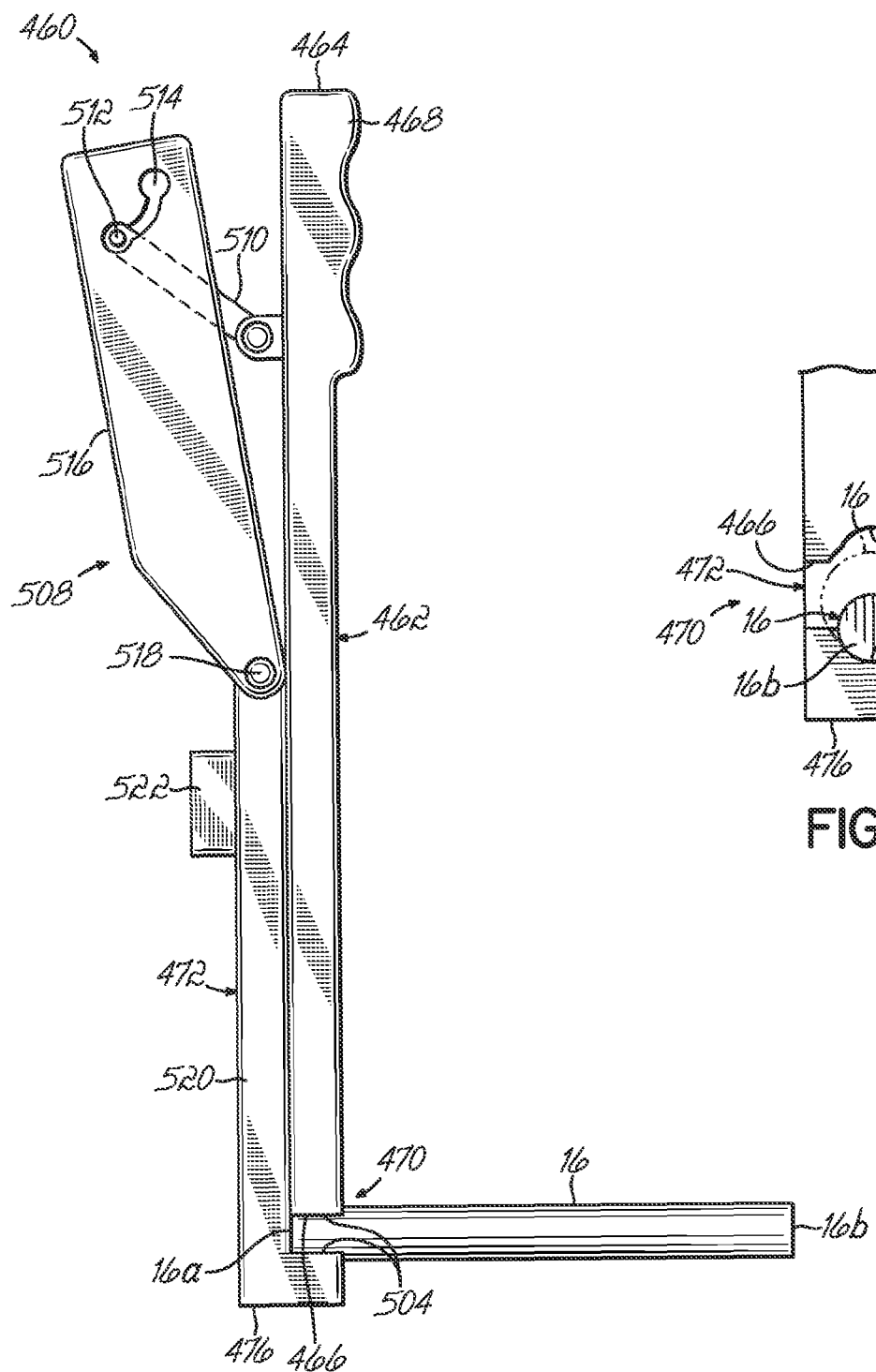
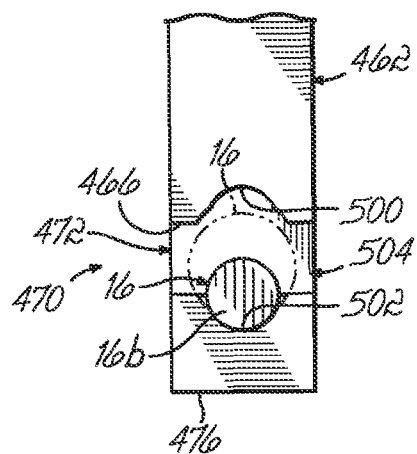
FIG. 15
FIG. 14

INSTRUMENTATION AND ASSOCIATED TECHNIQUES FOR MINIMALLY INVASIVE VERTEBRAL ROD INSTALLATION

BACKGROUND

This invention relates generally to spinal fixation surgery and more specifically relates to instrumentation and associated techniques for minimally invasive installation of vertebral connecting elements of spinal fixation constructs.

The human spinal column is a highly complex system of bones and connected tissues that provide support for the body and protects the delicate spinal cord and nerves. The spinal column includes a series of vertebrae stacked one atop the other. Each vertebral body includes a relatively strong cortical bone portion forming the outside surface of the body and a relatively weak cancellous bone portion forming the center of the body. An inter-vertebral disc is situated between each vertebral body that provides for cushioning and dampening of compressive forces applied to the spinal column. The vertebral canal containing delicate spinal cords and nerves is located just posterior to the vertebral bodies.

A variety of types of spinal column disorders may be caused by abnormalities, disease, trauma or the like and result in debilitating pain as well as diminished nerve function in many cases. One known technique to address many such spinal conditions is commonly referred to as spinal fixation. Surgical implants are used for fusing together and/or mechanically immobilizing adjacent vertebrae of the spine. Spinal fixation may also be used to improve the position of the adjacent vertebrae relative to one another so as to alter the overall alignment of the spine. Such techniques have been used effectively to treat many spinal conditions and to relieve pain suffered by the patient.

One particular spinal fixation technique includes immobilizing the spine by using connecting elements or orthopedic spine rods which run generally parallel to the spine. This is accomplished by exposing the spine posteriorly and fastening hooks, bone screws, or anchors to the pedicles of the appropriate vertebrae. The vertebral anchors are generally placed two per vertebrae, one at each pedicle on either side of the spinal column and serve as anchor points for the connecting elements or spine rods. The aligning influence of the rods forces the spine to conform to a more desirable shape. In many cases, the spine rods are bent to achieve the desired curvature of the spinal column.

Installation of such spinal fixation constructs conventionally requires a surgeon to prepare a long incision aligned with the spinal column of a patient. The pedicle screws, hooks or other vertebral anchors are then attached to a number of vertebrae after which the connecting element or spine rod is located with respect to saddles or U-shaped channels attached to the vertebral anchors. Conventional surgical methods require a large midline incision and retraction of skin, muscle and other tissue to provide the surgeon with sufficient visualization of the pedicle bone structure.

The accuracy of the placement and configuration of the spine fixation elements are very important. In combination with the relatively long incision typically required for the installation of the fixation construct, extended surgical procedures and related difficulties or complications are generally recognized as major contributing influences for extended patient recovery and less than optimal spinal fixation results. Therefore, surgical techniques and the associated instrumentation to accomplish more minimally invasive installation of the spinal fixation construct is highly desirable to avoid the problems associated with known surgical installation techniques.

SUMMARY OF THE INVENTION

This invention addresses these and other shortcomings in the prior art. The devices and methods associated with this invention are used to aid in the surgery and installation of vertebral fixation components, particularly the connecting element or spinal rod.

As is common in many spinal fixation systems, vertebral anchors such as pedicle screws are inserted into the target vertebrae of a patient's spinal column. The spinal fixation system typically includes a connecting element joining at least two vertebral anchors to provide added support and a degree of rigidity to the patient's spine. The connecting element may be a rigid spine rod that is generally linear or shaped, as appropriate, or the connecting element may be a less rigid structure. Nevertheless, installation of the connecting element to the vertebral anchors coupled to the respective vertebrae is facilitated through a minimally invasive surgical procedure according to various embodiments of this invention.

In one aspect, this invention is directed to a tool for manipulating the connecting element of the spinal fixation system relative to the vertebral anchors. The tool includes a first elongate member having proximal and distal ends in which the distal end is configured for insertion through an incision in a patient for placement proximate one of the vertebral anchors coupled to a vertebrae of the spinal column. A handle is provided proximate the proximal end of the elongate member and configured to be grasped by a surgeon for manipulation of the tool. A connecting element retainer is provided proximate the distal end of the elongate member. The retainer is configured to selectively hold the connecting element for insertion through the incision in an orientation generally perpendicular to the spinal column and subsequent subcutaneous reorientation generally parallel to the spinal column. In another aspect of this invention, a pivoting mechanism is included on the elongate member and is configured to reorient the connecting element relative to the longitudinal axis of the elongate member for installation of the connecting element onto the vertebral anchors after insertion through the incision.

The tool may include a second elongate element pivotally coupled to the first elongate element at a medial position between the distal and proximal ends of the first elongate element. The second elongate element may also include a handle configured for grasping and manipulation by the surgeon. The first and second elongate element may be coupled together in a scissor-like fashion according to various embodiments of this invention.

A passage may be included at a distal end of one of the elongate elements is configured to allow installation of the connecting element through the passage. The connecting element retainer is provided on the other elongate element and through manipulation of the handles the connecting element is forced through the passage and into the vertebral anchors for secure attachment.

In other aspects and embodiments of this invention, a lever is coupled to the elongate member and is adapted to actuate the pivotal movement of the connecting element via the connecting element retainer for appropriate positioning and subsequent installation to the vertebral anchors.

Other embodiments of this invention utilize a connecting element retainer on the elongate member which is adjustable to accommodate a range of sizes of the connecting element while still holding and retaining the connecting element for proper positioning and installation with respect to the vertebral anchors. In some aspects of this invention, a clamp is configured to selectively retain one end of the connecting element and utilizes a jaw positioned proximate the distal end of the elongate member. The jaw is movable relative to the elongate member and may include a multi-bar linkage to provide for a variety of clamping force parameters to accommodate a variety of connecting elements and associated installation requirements.

In other embodiments of this invention, an extension member is configured to be selectively coupled to one of the vertebral anchors to provide percutaneous access to the vertebral anchor when coupled thereto. The tool kit for manipulating the connecting element into position relative to the vertebral anchors may include not only the extension member mounted to the vertebral anchors but also the connecting element installation tool. The extension member may include a lumen axially aligned with the vertebral anchor to pass a set screw or other components to the vertebral anchor for installation of the connecting element. A recess may be provided on the extension member which is offset from the primary lumen and configured to direct and guide the connecting element installation tool and the connecting member to the vertebral anchors.

The various embodiments of this invention enable the surgeon to install the spinal fixation construct with smaller discrete incisions as opposed to an extended incision. As such, a more minimally invasive surgical procedure can be accomplished with this invention thereby promoting patient recovery post-surgery. As a result of these and other aspects of this invention, increased efficiency and accuracy is provided for installation of a spinal fixation construct in a minimally invasive atmosphere thereby promoting patient recovery and optimum spinal surgery results.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 14 is a view similar to FIG. 13 with the installation tool engaged with the spine rod;

FIG. 15 is a front elevational partial view of the embodiment of FIGS. 13-14 with the tool adapted to engage a range of spine rod sizes;

DETAILED DESCRIPTION OF THE INVENTION

Figure 3:
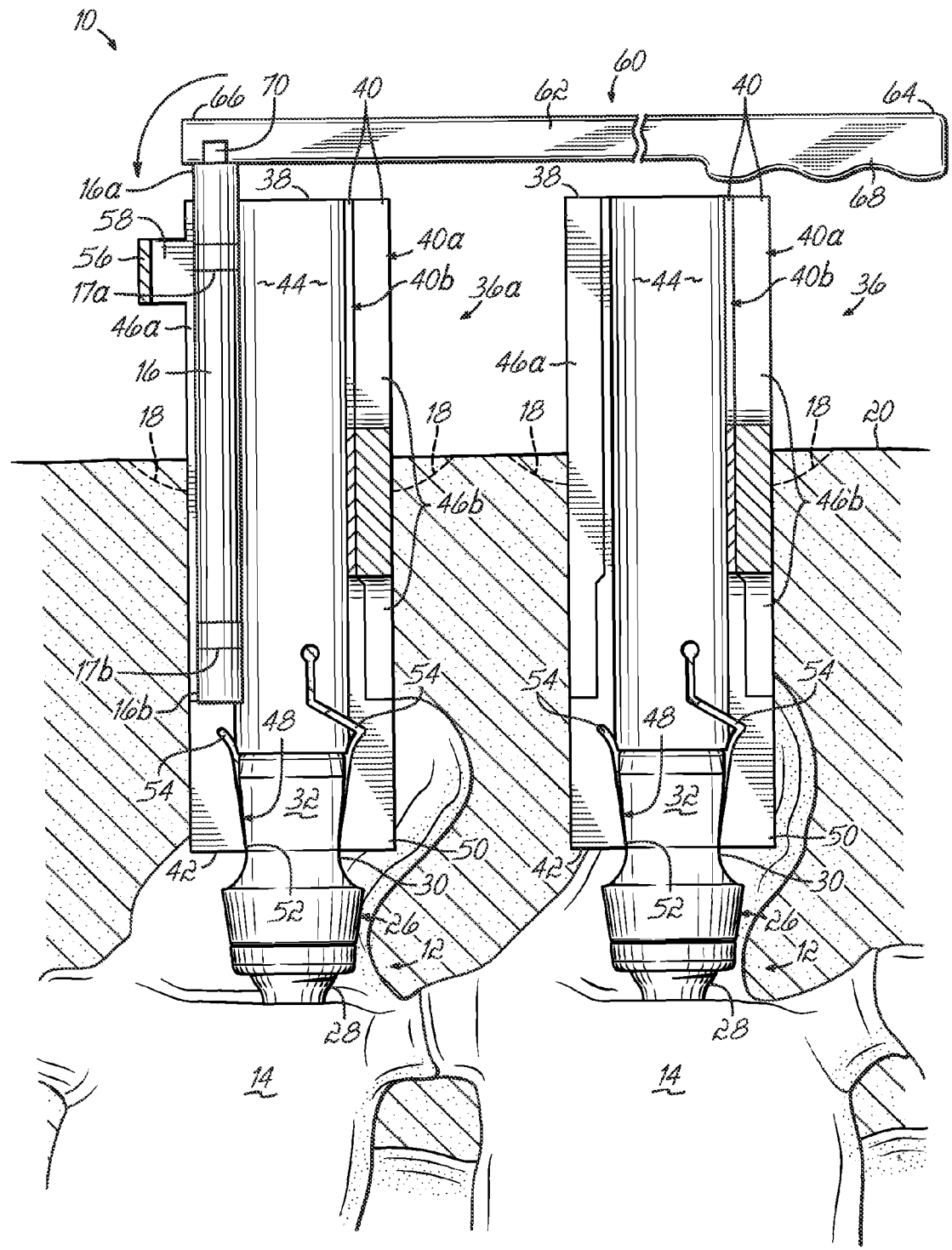
FIG. 3 is a side elevational view, partially in cross-section, of a spinal fixation construct including a pair of extension members and vertebral anchors as shown in FIGS. 1-2 being surgically implanted in selected vertebrae of a patient's spine utilizing an installation tool according to a first embodiment of this invention.

Referring to the drawings, various embodiments of spine rod or connecting element installation tools to assist in a minimally invasive surgery to install a spinal fixation construct and associated installation methods are shown. In FIG. 3, an exemplary spinal fixation construct 10 includes a number of vertebral anchors 12 which in one embodiment are each pedicle screw assemblies, each of which is inserted into selected vertebrae 14 of a patient. The pedicle screw assemblies 12 are joined together in the spinal fixation construct by a connecting element 16 which in one embodiment is a spine rod. The connecting element 16 may be something other than a rigid rod according to alternative embodiments of this invention. According to various aspects of this invention, the individual pedicle screw assemblies 12 may be inserted into the patient through discrete and often individual incisions 18 in the patient's skin 20. In certain instances, a single incision 18 such as a minimally invasive incision may be available to provide installation of multiple pedicle screw assemblies 12 in adjacent vertebrae 14. The small, discrete incisions 18 provide the opportunity for insertion of a cannulated pedicle screw via a K-wire (not shown) inserted through the incision 18 to the precise location on the vertebrae 14 for proper installation of the pedicle screw 12. While cannulated and other pedicle screw assemblies are contemplated and described herein, one of ordinary skill in the art will appreciate that other types of vertebral anchors and vertebrae engaging mechanisms can be utilized such as hooks for anchoring the connecting element 16 to the patient's spinal column.

Figure 1:
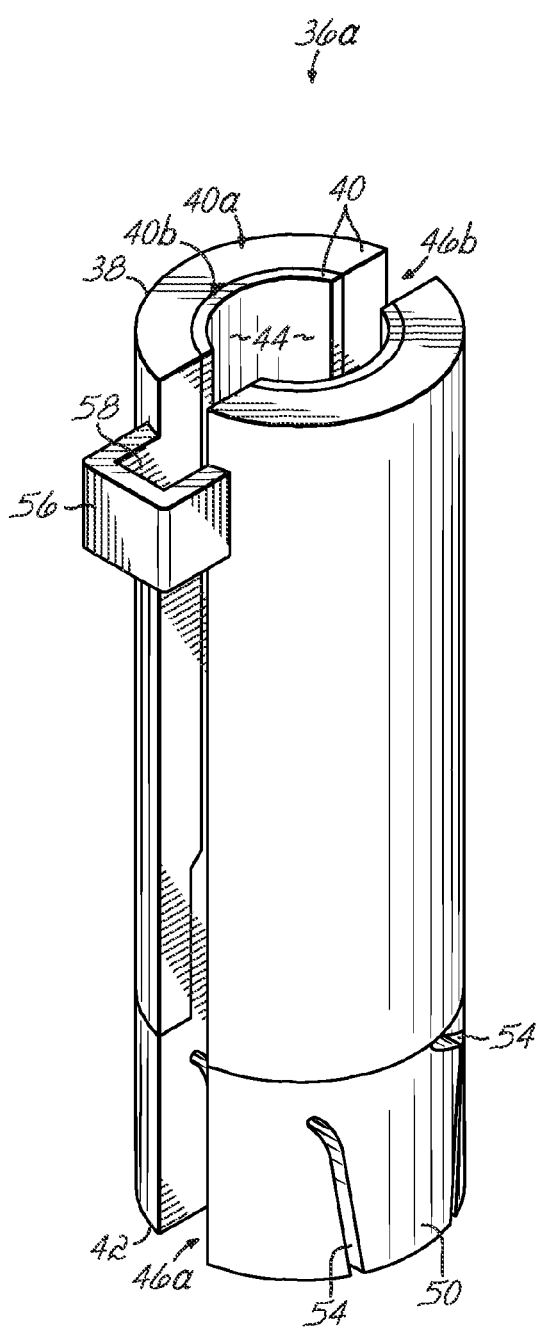
FIG. 1 is a perspective view of a vertebral anchor extension member utilized in a spinal fixation construct according to various embodiments of this invention.
Figure 2:
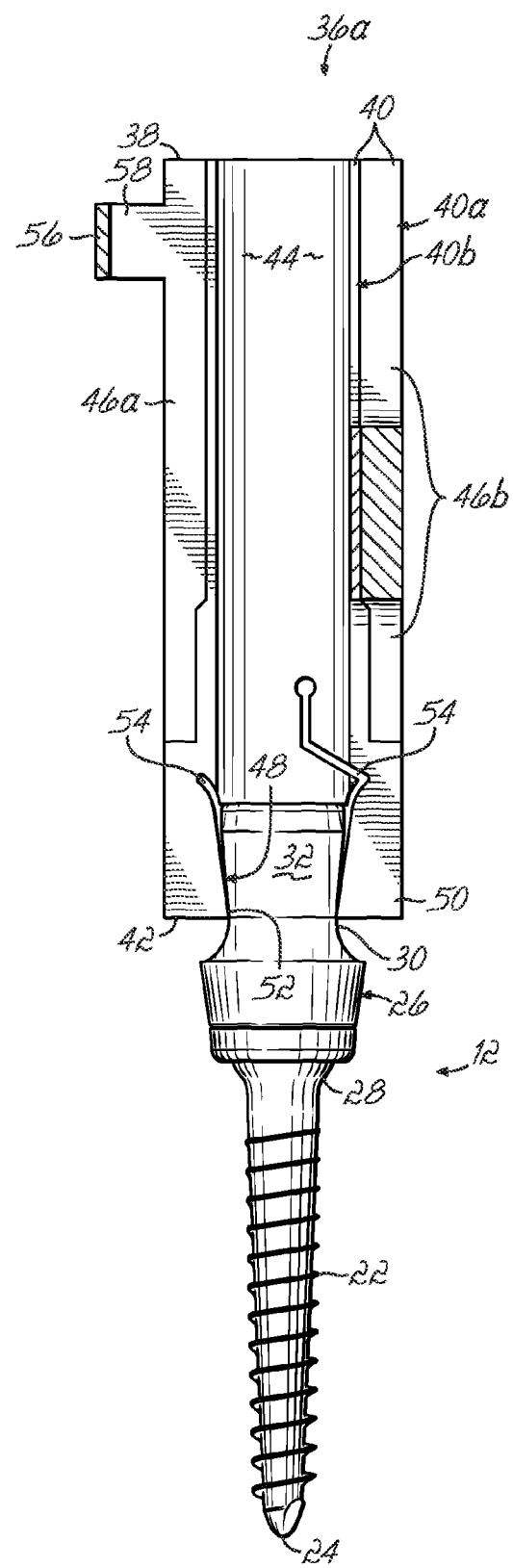
FIG. 2 is a side elevational, partially in cross-section, of the extension member of FIG. 1 mounted upon an exemplary vertebral anchor.

As shown generally in FIGS. 1-3, the vertebral anchor 12 according to one embodiment of this invention includes a pedicle screw 12 having a threaded shaft 22 and a distal tip 24 for insertion and stable positioning into the pedicle area of the patient's vertebrae 14. The pedicle screw 12 shown herein is a polyaxial pedicle screw in which a polyaxial body 26 mounted opposite from the distal tip 24 of the screw 12 to a screw head 28 provides for a variety of orientations of the polyaxial body 26 relative to longitudinal axis of the screw 12 as is common with many pedicle screw systems. The polyaxial body 26 coupled to the pedicle screw head 28 includes a saddle or U-shaped channel 30 (FIG. 4) formed between a pair of spaced arms 32 extending upwardly. The polyaxial body 26 is adapted to receive the spine rod 16 in the saddle or U-shaped channel 30 and the spine rod 16 is securely retained by the polyaxial body 26 via a fastener such as a set screw 34 (FIG. 5) threadably received therein as is common with many known pedicle screw systems.

The various embodiments of this invention may be used in conjunction with an extension member 36 projecting upwardly from the vertebral anchor polyaxial head 26 as shown in FIGS. 1-5. Examples of such extension members are disclosed in U.S. patent application Ser. No. 11/567,238, filed Dec. 6, 2006, assigned to the assignee of this invention and hereby incorporated by reference entirely. Exemplary extension members 36 for use on the vertebral anchors 12 are shown herein with certain features, but other configurations and designs are readily utilized with this invention. The extension members 36 project through the incision 18 such that a distal end 38 of the members 36 is located percutaneously above the patient's skin 20 when the anchor 12 is inserted into the vertebrae 14 as shown in FIG. 3.

Embodiments of extension members 36 according to this invention are shown particularly in FIGS. 1-5. The extension members 36 are each elongate and adapted to extend percutaneously from the body when the anchor 12 is secured to the patient's vertebrae 14. The elongate extension member 36 may include an elongate tubular sleeve having a generally arcuate sidewall 40 with a generally circular cross-sectional configuration. The extension member 36 has a first more proximal end 42 adapted to be coupled to the anchor head 26 and the second or distal end 38 adapted to be positioned percutaneously for access to the anchor head 26 through a primary lumen 44 formed by the arcuate sidewall 40 of the extension member 36. Other shapes of lumen 44, such as square, oval or rectangular, may be used to provide access to the anchor head 26. As shown in FIG. 1, the extension member 36 includes slots 46a, 46b positioned diametrically opposite from one another.

Referring particularly to FIGS. 2 and 3, a socket 48 is formed on the interior of a flange 50 on the proximal end 42 and is sized and configured to mate with the anchor head 26 when the extension member 36 is mounted to the anchor 12. In one embodiment of the invention, the socket 48 has a generally upwardly tapered configuration with a throat or entry region 52 being more narrow than the upper portion of the socket 48. This contour corresponds generally to the contour of the anchor head 26 thereby providing a snug and secure mating relationship as shown generally in FIGS. 2-3.

Figure 5:
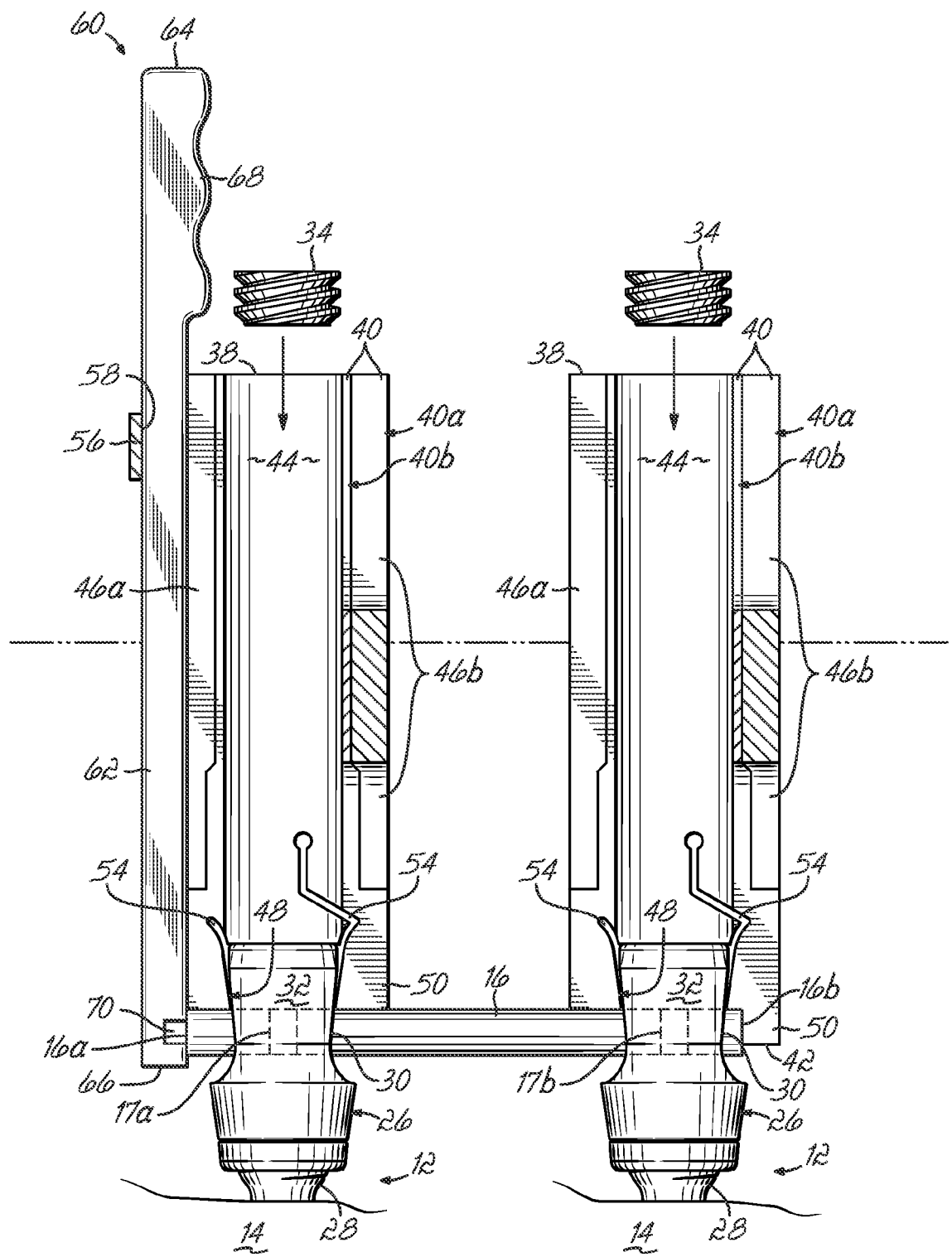
FIG. 5 is a view similar to FIG. 3 with the spine rod installed and being secured to the vertebral anchors by associated set screws.

One aspect of the extension member 36 according to this invention is one or more slits 54 in the flange 50 which allow the flange 50 to temporarily expand or deform while the extension member 36 is being coupled to or uncoupled from the anchor 12. As shown most clearly in FIGS. 2-3, the flange 50 includes a number of the slits 54. In alternative embodiments, any number and/or configuration of sized or shaped slits can be used to provide for the desired deflection characteristics. The slits 54 allow the flange 50 of the extension member 36 to temporarily expand as the throat 52 of the extension member 36 passes over the outwardly tapered distal portion of the anchor head 26. Continued downward movement of the extension member 36 allows the larger diameter portion of the anchor head 26 to enter into the larger diameter portion of the socket 48 in the flange 50 and the reduced neck region of the anchor head 26 seats within the reduced diameter throat 52 of the flange 50. The slits 54 allow the flange 50 to expand outwardly until the anchor head 26 is seated within the socket 48 as shown in FIG. 5. At that time, the slits 54 allow the flange 50 on the extension member 36 to relax into a mating configuration with the anchor head 26. The extension member 36 may have a telescoping construction such that an outer sleeve 40a is slidable relative to an inner sleeve 40b. The outer sleeve 40b, when coupled to the inner sleeve 40a as shown in FIG. 3, restricts the expansion of the slits 54.

While the anchor head 26 and the socket 48 are shown and described as having tapered, mating configurations, other configurations and designs are envisioned within the scope of this invention to provide a selectively retained fit between the extension member 36 and the anchor head 26.

Similar to other previously described embodiments of this invention, once the extension member 36 is seated on the anchor head 26, various components may be inserted through the lumen 44 formed in the extension member 36 toward the anchor head 26 for installation onto the vertebral anchors 12 on the spinal fixation construct 10. The set screw 34 may be inserted through the lumen 44 for mating with the anchor 12 as shown in FIG. 5.

An alternative embodiment of an extension member 36a according to this invention is shown in FIGS. 1-3 and includes a generally U-shaped member 56 that acts as a guide and is positioned near the distal end 38 of the extension member 36a at a radial or laterally offset position on an outer side of the sidewall 40. The U-shaped member 56 defines a recess 58 which is aligned in an offset relationship from the longitudinal axis of the extension member 36a and the lumen 44. The U-shaped member 56 can be formed only at the distal end 42 of, along a portion of, or from the distal end 42 to the proximal end 38 of the extension member 36, 36a. The recess 58 defined by the U-shaped member 56 allows for a connecting element, such as the spine rod 16, to be inserted along with an associated connecting element insertion tool 60 through the incision 18. Advantageously, the recess 58 provides a guide offset from the lumen 44 to direct the position of the connecting element 16 without obscuring the lumen 44 of the extension member 36 to provide visualization of the placement of the rod 16 and so that the other components, such as the set screw 34, may be inserted through the lumen 44 to the vertebral anchors 12 without requiring removal of rod 16 insertion instrumentation. The recess 58 may also provide for instrumentation to be passed and removed at any time throughout the spinal construct installation procedure.

Figure 4:
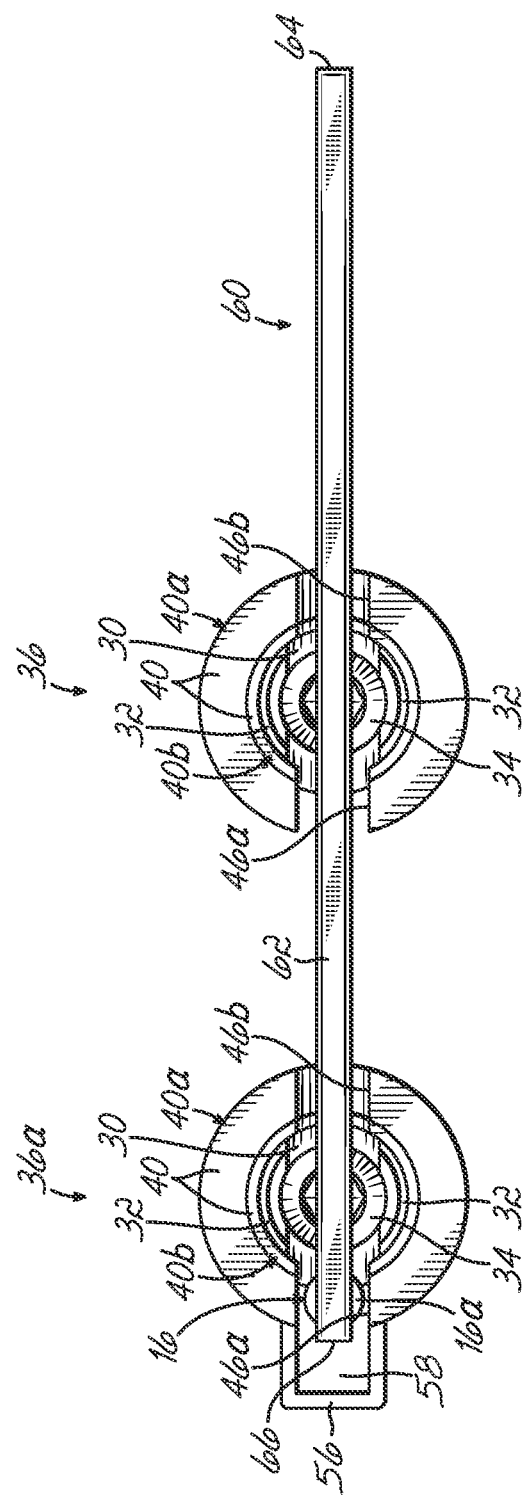
FIG. 4 is a top view of the arrangement shown in FIG. 3.

One embodiment according to this invention of a connecting element installation tool 60 is shown in FIGS. 3-5. The installation tool 60 includes an elongate member 62 having a proximal end 64 spaced from a distal end 66. The tool 60 includes a handle 68 configured to be grasped by the surgeon for manipulation of the tool 60. The handle 68 is located at the proximal end 64 of the elongate member 62. A connecting element retainer 70 is located proximate the distal end 66 of the elongate member 62 and is configured to selectively retain the connecting element, spine rod 16 or other component of the spinal fixation construct 10 for insertion through the incision 18 and toward the vertebral anchors 12. The connecting element retainer 70 according to this embodiment of the tool 60 holds one end 16a of the connecting element or spine rod 16 so that the elongate member 62 of the tool 60 is generally perpendicular to the orientation of the spine rod 16. As such, the spine rod 16 is initially inserted through the incision 18 relative to the recess 58 of the extension member in a direction generally parallel with the axis of the primary lumen 44 and may be laterally offset from the lumen 44 as shown in FIGS. 3 and 4. Once the leading end 16*b* of the spine rod 16 mounted on the installation tool 60 reaches the vertebral anchor 12, the spine rod 16 and installation tool 60 are reoriented in the direction of arrow A of FIG. 3. Available space and access for the reorientation procedure is provided by the slots 46 of the extension members 36 and the recess 58. Advantageously, once the spine rod 16 is inserted through channels 30 of the heads 26 of the vertebral anchor 12 and seated relative to the vertebral anchors 12, the installation tool 60 may be positioned in the recess 58 as shown in FIG. 5 so that set screws 34 or other components of the spinal fixation construct 10 may pass through the lumen 44 of the extension member 36 for direct access to the vertebral anchor heads 26 and secure retention of the connecting element or spine rod 16 relative to the vertebral anchor heads 26. Once the connecting element 16 is appropriately positioned and/or secured to the vertebral anchors 12, the installation tool 60 can be disengaged from the spine rod 16 for removal from the patient and the extension member 36, 36*a*.

Figure 6:
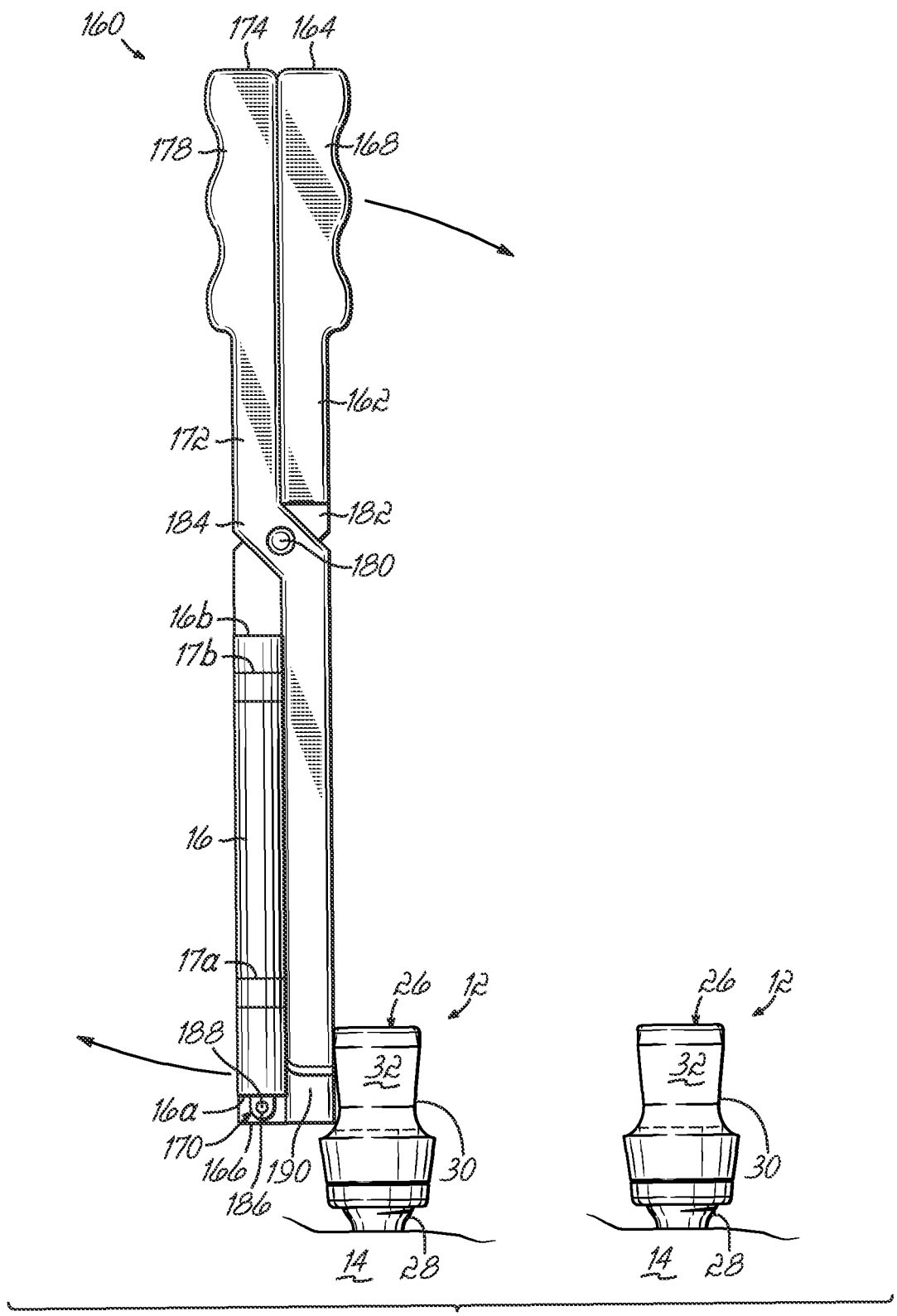
FIG. 6 is a side elevational view of an installation tool according to a second embodiment of this invention delivering a spine rod to a pair of vertebral anchors inserted in respective vertebrae.
Figure 7:
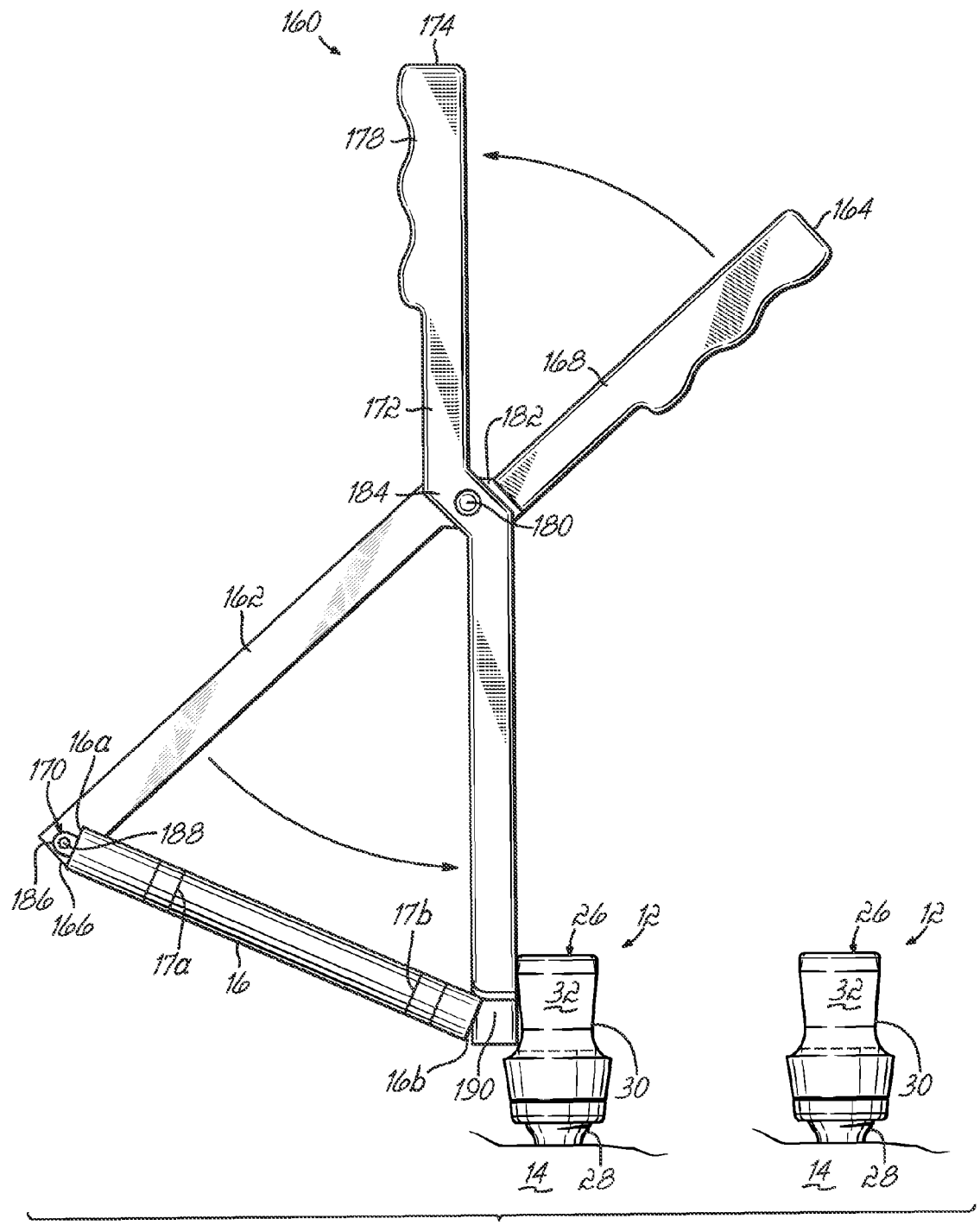
FIG. 7 is a view similar to FIG. 6 with the installation tool preparing to insert the spine rod into the vertebral anchors.
Figure 8:
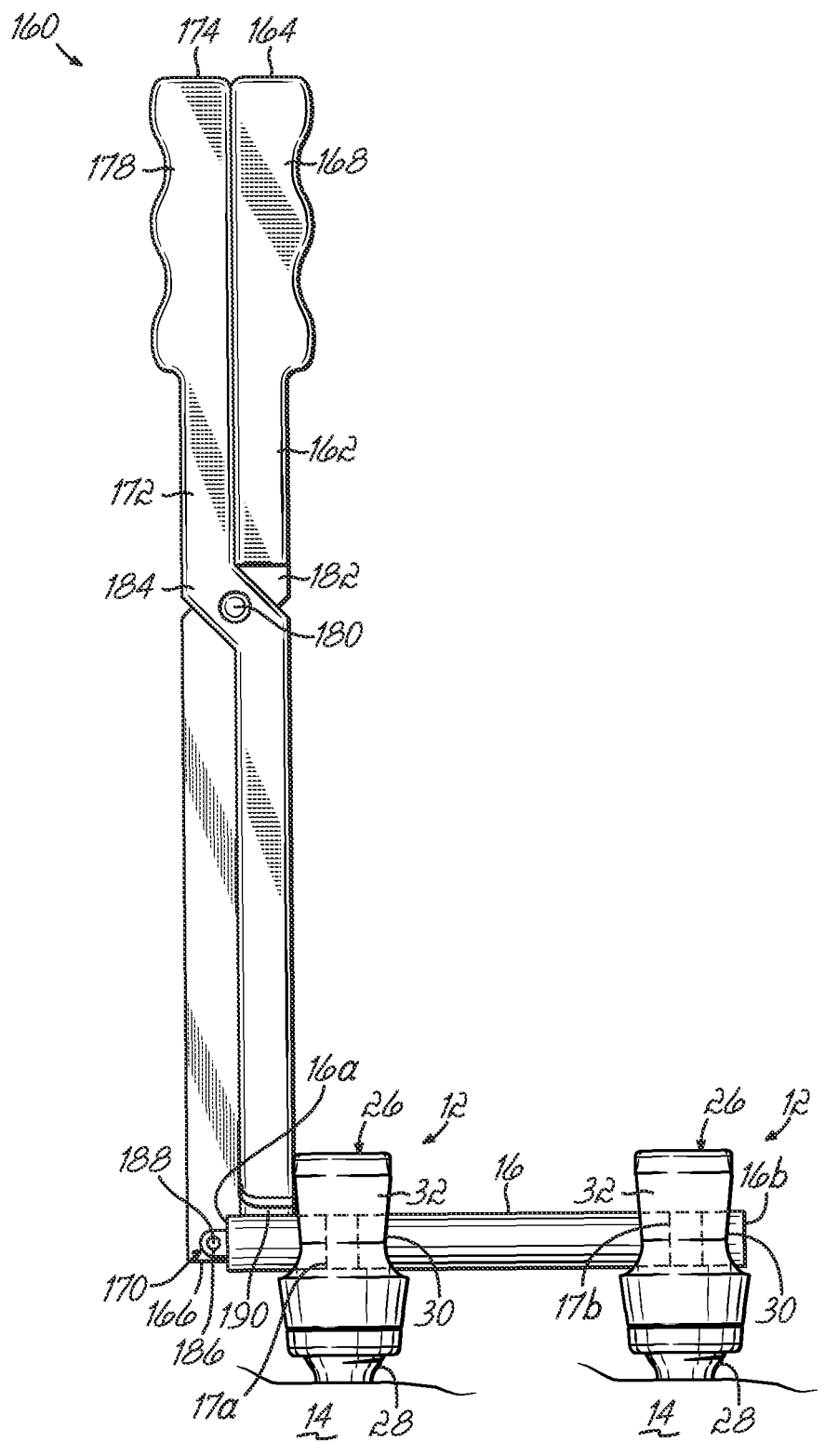
FIG. 8 is a view similar to FIG. 7 with the spine rod installed in position relative to the vertebral anchors.

Another embodiment of a connecting element installation tool 160 according to this invention is shown in FIGS. 6-8 in which components of the invention which are the same as or similarly corresponding components in other embodiments of this invention are identified by the same or similar reference numerals. The installation tool 160 according to this embodiment includes the elongate member 162 having a proximal end 164 spaced from a distal end 166 and a handle 168 located at the proximal end 164 of the elongate member 162 for manipulation of the tool 160. A second elongate member 172 also having a proximal end 174 spaced from a distal end 176 and a handle 178 located at the proximal end 174 is also includes in this embodiment. The two elongate members 162, 172 are pivotally coupled together by a pin 180 located between the proximal and distal ends of the members. Each of the elongate members includes a jog 182, 184 at which the pivot pin 180 coupling the members 162, 172 together is positioned. As such, the installation tool 160 according to this embodiment is a scissor-like instrument such that movement of the proximal ends 164, 174 of the members 162, 172 toward and away from each other likewise moves the distal ends 166, 176 of the members 162, 172 toward and away from each other.

As shown in FIG. 6, the connecting element 16 is held by the installation tool 160 by the connecting element retainer 170 located at the distal end 166 or 176 of one of the elongate members 162 or 172. The retainer 170 of this embodiment 160 is combined with a pivoting mechanism 186 and the combination includes a pivot pin or set screw 188 at the distal end 166 of the elongate member 162. The connecting element 16 is generally aligned with the longitudinal axis of the installation tool 160 as shown in FIG. 6 for insertion through the incision 18 relative to the extension member 36 on one of the vertebral anchors 12. For simplicity and clarity, the extension members 36 are omitted from FIGS. 6-8, but it should be readily appreciated that the installation tool 160 according to this and other embodiments of this invention shown and described herein are capable of being used in combination with the extension members 36 as with the embodiment 60 shown in FIGS. 3-5.

The installation tool 160 is inserted through the incision 18 toward the vertebral anchor 12 in a collapsed configuration as shown in FIG. 6 with the connecting element 16 generally aligned with the longitudinal axis of the installation tool 160.

Once the installation tool 160 and connecting element 16 are positioned as shown in FIG. 6, the handles 168, 178 at the proximal end of the tool 160 are separated as is the distal ends 166, 176 of the elongate members 162, 172 as shown in FIG. 7. Coincident with the separation of the ends of the installation tool 160, the connecting element 16 pivots via the pivot mechanism 186 downwardly to a position shown in FIG. 7. With the distal end 176 of the second elongate member 172 juxtaposed to the vertebral anchor head 26, the free end 16*b* of the connecting element 16 is aligned with a passage 190 in the distal end 166 of the first elongate member 162. To maneuver the rod 16 into its position as shown in FIG. 7, a separate instrument (see FIGS. 13-17) may be utilized alone or in conjunction with the installation tool 160 to apply force on the free end 16*b* of the rod 16 until it is positioned in a proper orientation as shown in FIG. 7.

With the connecting element 16 positioned as shown in FIG. 7, the handles 168, 178 of the installation tool 160 are squeezed together such that the proximal ends 164, 174 are forced together as are the distal ends 166, 176 of the tool 160. The connecting element 16 as such will then pierce through the tissues between the pedicle screws 12 until the handles 168, 178 are juxtaposed against each other and the installation tool 160 is closed and the connecting element 16 is inserted into the channels 30 of the vertebral anchor heads 26 as shown in FIG. 8. Once the connecting element 16 is positioned in the vertebral anchor heads 26, the installation tool 160 is disengaged from the connecting element by, for example, unscrewing the set screw or pin 188 at the distal end of the elongate member. Advantageously, the set screw 188 is positioned in an orientation that is accessible and visible through the extension member 36 in the configuration of FIG. 8.

In the exemplary embodiments shown herein, the connecting element 16 may include markings 17*a*, 17*b* to identify the proper positioning of the connecting element 16 within vertebral anchors 12. The markings 17*a*, 17*b* allow for visualization of the proper alignment of the connecting element 16 through a lumen in a percutaneous extension member, like through the lumen 44 in extension member 36. In alternative embodiments, the connecting element 16 can include a single marking that assists in identifying the proper location of the connecting element 16 within the vertebral anchors 12. The marking can be formed into the connecting member or added onto the surface of the connecting element.

Figure 9:
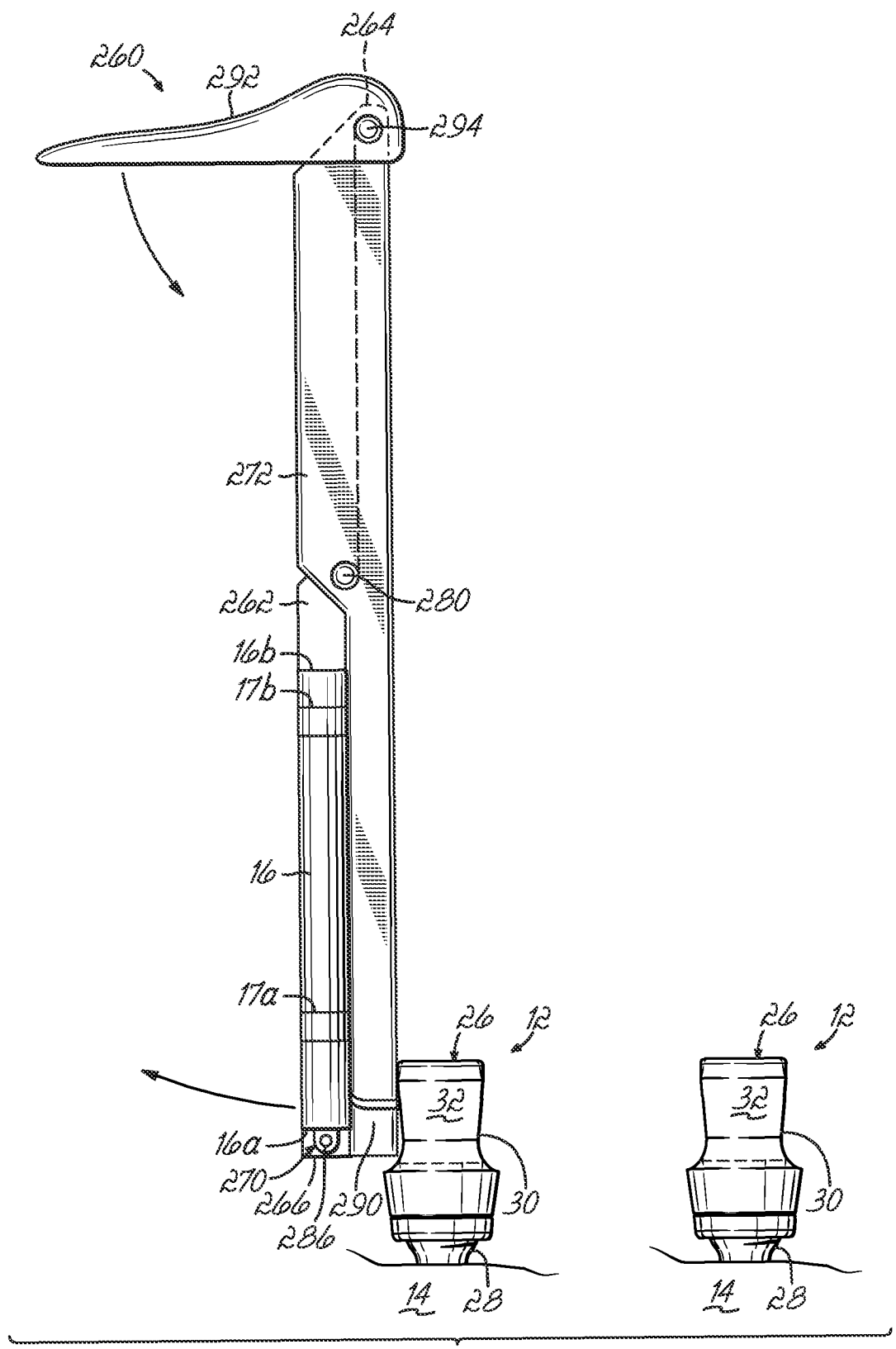
FIG. 9 is a side elevational view of an installation tool according to a third embodiment of this invention delivering a spine rod to a pair of vertebral anchors inserted in respective vertebrae.
Figure 10:
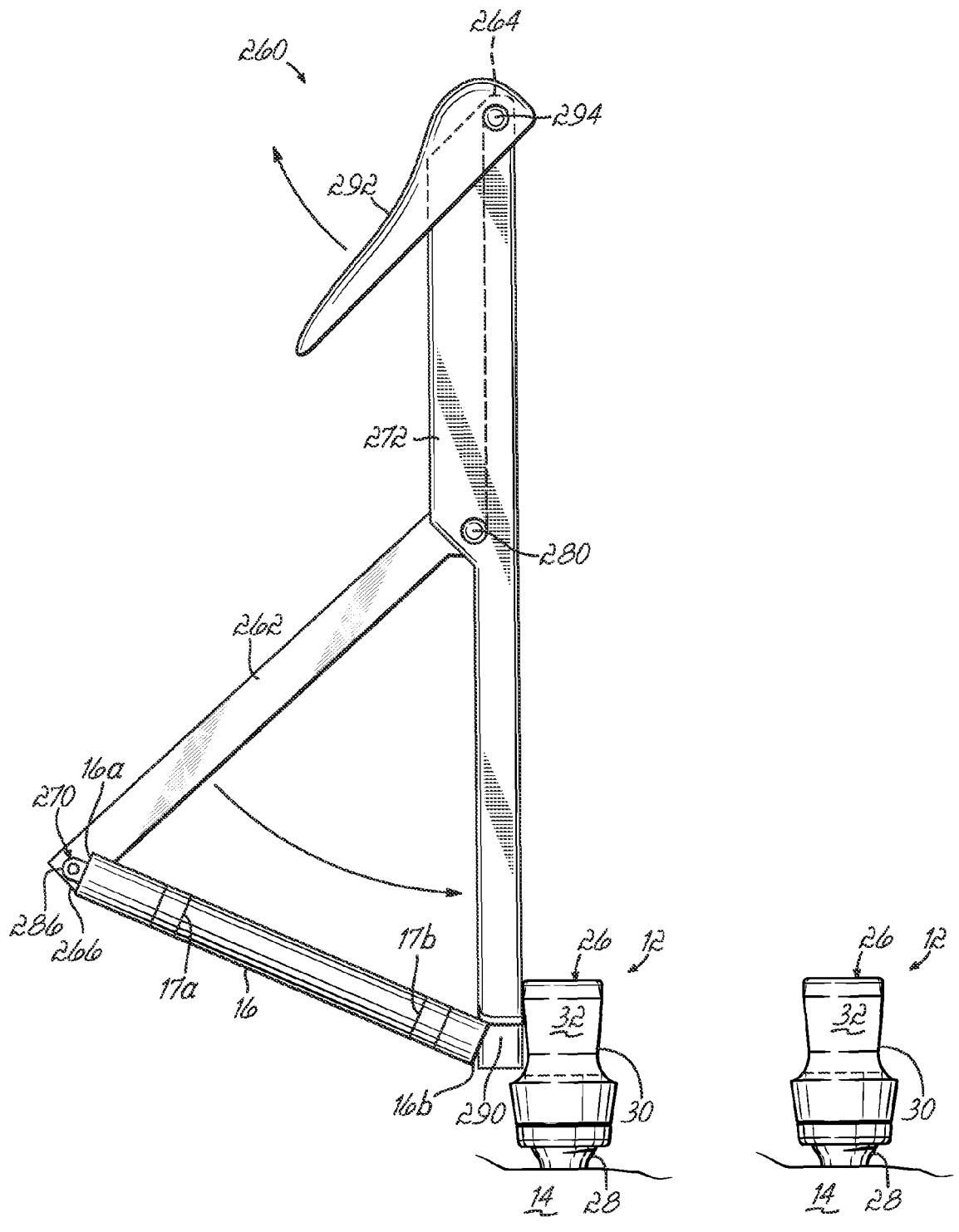
FIG. 10 is a view similar to FIG. 9 with the installation tool preparing to insert the spine rod into the vertebral anchors.
Figure 11:
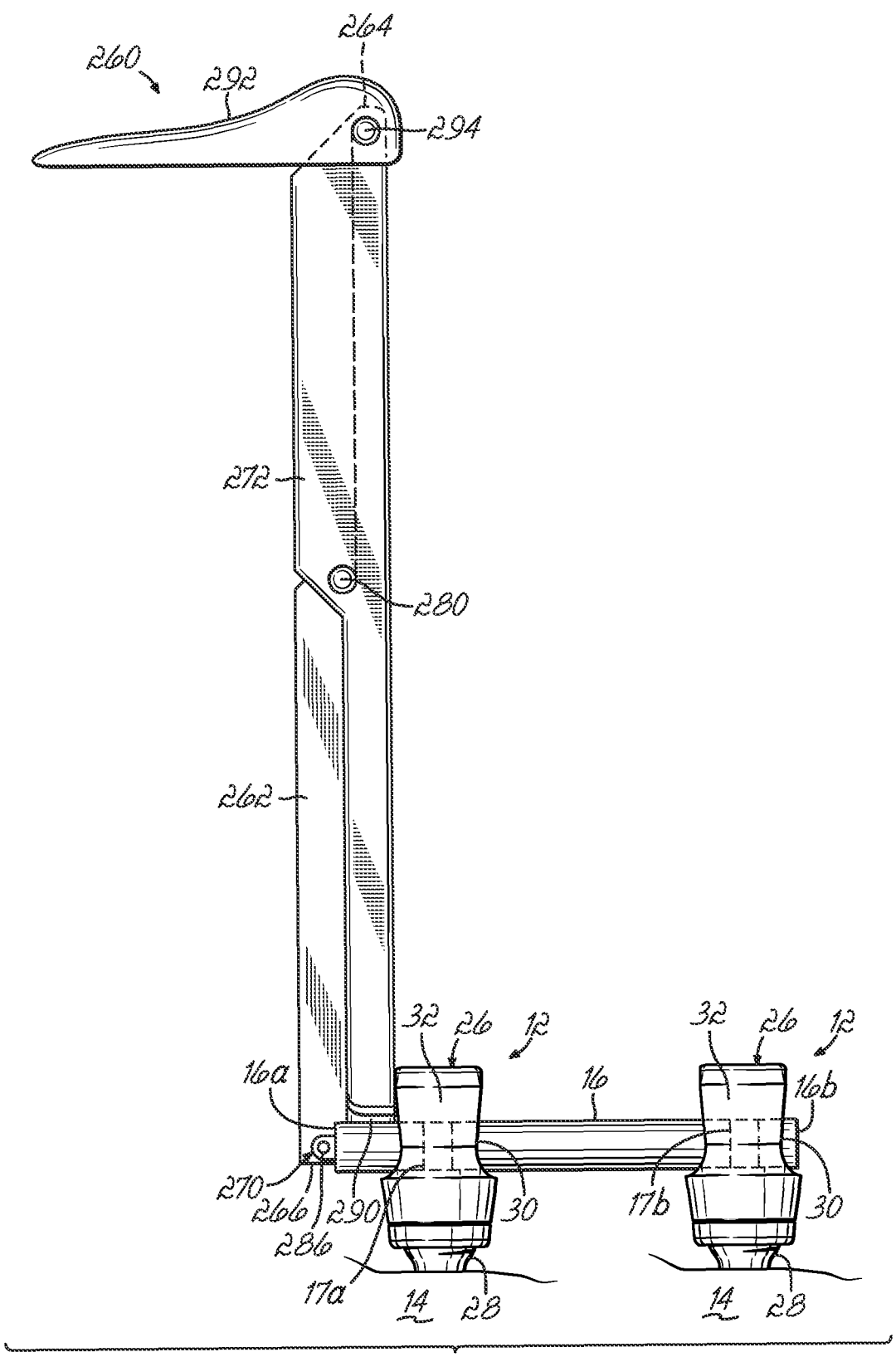
FIG. 11 is a view similar to FIG. 10 with the spine rod installed in position relative to the vertebral anchors.

A further alternative embodiment of the installation tool 260 and associated installation technique is shown in FIG. 9-11 in which the installation tool 260 includes the first elongate member 262 in which the connecting element retainer 270 and associated pivoting mechanism 286 are provided on the distal end 266 of the member 262. The second elongate member 272 includes the passage 290 proximate its distal end 276 and the two members 262, 272 are pivotally joined together at a pivot point 280 medially positioned on the second elongate member 272. A lever 292 is pivotally mounted at the proximal end 264 of the installation tool 260. The elongate members 262, 272 are generally aligned along the longitudinal axis of the installation tool 260 along with the connecting element 16 for insertion through the incision 18 and positioning relative to the vertebral anchor head 26 as shown in FIG. 9.

With the components in this configuration, the lever 292 is forced downwardly toward the remainder of the elongate members about a pivot pin 294. The lever 292 controls the opening and closing of the distal ends 266, 276 of the instrument 260 such that downward motion of the lever 292 forces the distal ends apart from the configuration shown in FIG. 9 resulting in the configuration shown in FIG. 10 with the connecting element 16 pivoted downwardly with the free end 16b of the connecting element 16 positioned for entry into and through the passage 290 and subsequently the channels 30 of the vertebral anchor heads 26. An additional tool (see FIGS. 13-17) may be utilized to reposition the connecting element 16 from the orientation shown in FIG. 9 to the orientation shown in FIG. 10.

With the connecting element 16 poised for insertion into the vertebral anchor channels 30 as shown in FIG. 10, the lever 292 is pulled upwardly by the surgeon to thereby collapse the distal ends 266, 276 of the installation tool 260 and force the connecting element 16 through the passage 290 and into the channels 30 of the vertebral anchor heads 26 resulting in positioning of the connecting element 16 as shown in FIG. 11. Once again, access to the connecting element retainer 270 is provided through the extension members 36 to release the connecting element 16 from the installation tool 260 so that the installation tool 260 can then be removed. Set screws 34 will then be installed on the vertebral anchors through the lumen 44 of the extension members 36 similar to the operation shown in FIG. 5.

Figure 12:
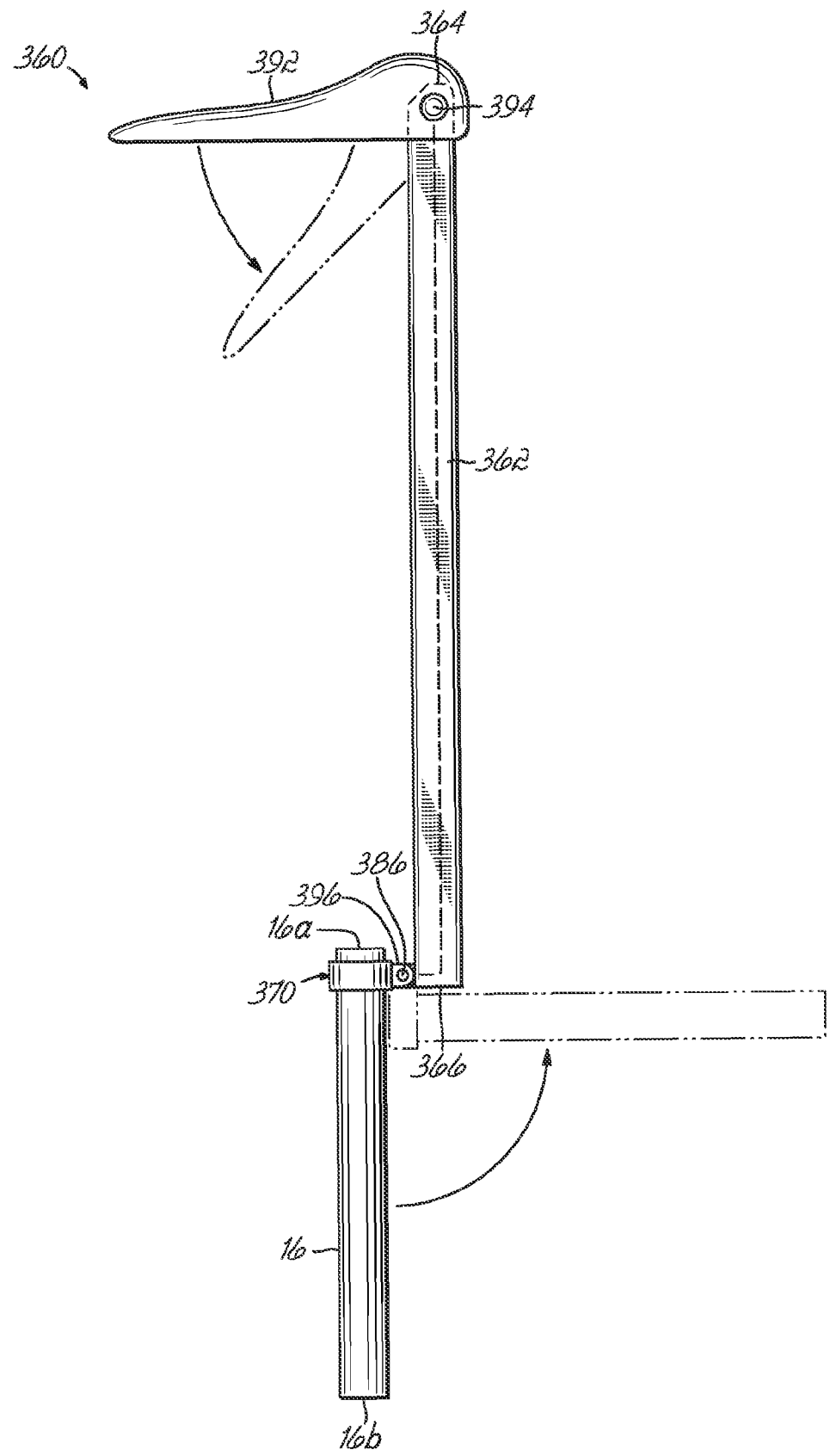
FIG. 12 is a side elevational view of an installation tool according to a fourth embodiment of this invention adapted to deliver a spine rod to vertebral anchors inserted in respective vertebrae.

A further alternative embodiment of an installation tool 360 according to this invention is shown in FIG. 12. The elongate member 362 includes a hinge 396 for the connecting element retainer 370 at the distal end 366. The hinge 396 couples a collar 398 and provides the pivoting mechanism 386 for reorienting the connecting element 16 retained by the collar 398 from a generally vertical position as shown in FIG. 12 to a horizontal position as shown in phantom lines in FIG. 12. The lever 392 at the proximal end 364 of the elongate member 362 controls the orientation of the connecting element 16 and rotation of the hinge 396. This allows the connecting element 16 to be introduced through the incision 18 and extension member 36 to the vertebral anchor 12 in a vertical orientation generally aligned with the longitudinal axis of the installation tool 360. The connecting element 16 is then rotated into a generally perpendicular orientation relative to the elongate member 362 for insertion into the channels 30 of the vertebral anchor heads 26. Once positioned in the generally horizontal orientation shown in phantom lines in FIG. 12, the collar 398 is disengaged from the connecting element 16 and the installation tool 360 is removed from the extension members 36 and the incision 18. The connecting element 16 is then secured to the vertebral anchors 12 by the insertion of the set screws 34 through the lumen 44 of the extension members 36 as shown generally in FIG. 5.

Figure 13:
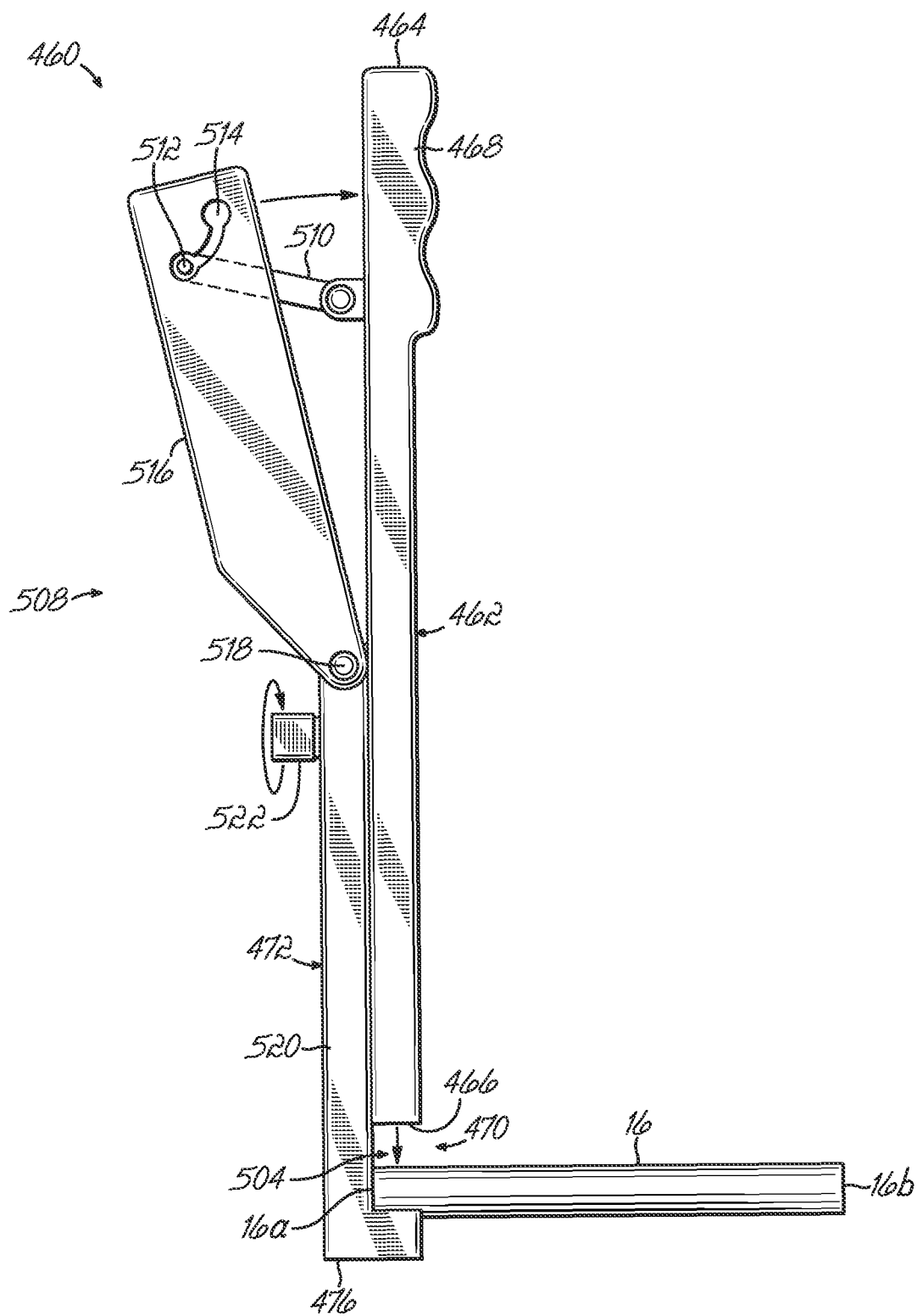
FIG. 13 is a side elevational view of an installation tool according to a fifth embodiment of this invention adapted to manipulate a spine rod into vertebral anchors inserted in respective vertebrae.

In another aspect of this invention, a tool 460 for manipulating a component of a spinal fixation construct 10 such as the spine rod or connecting element 16 into position relative to the vertebral anchors 12 is disclosed in FIGS. 13-15. The tool 460 according to this aspect of the invention includes a first elongate member 462 having a proximal end 464 spaced from a distal end 466 with a handle 468 located at the proximal end 464 and configured to be grasped by a surgeon. A retainer 470 is positioned proximate the distal end 466 of the elongate member and is adapted to selectively hold the component such as the spine rod 16 for installation onto one of the vertebral anchors 12. The retainer 470 in the embodiment shown in FIGS. 13-15 is adjustable to accommodate a range of sizes of the component as shown in FIG. 15. The distal end 466 of the elongate member 462 may include a generally arcuate recess 500 which cooperates with a corresponding recess 502 in a jaw 504 positioned in opposition to the distal end 466 of the elongate member 462 to form a clamp for retaining the spine rod 16. The jaw 504 is formed at a distal end 476 of a multi-bar linkage 508 which is pivotally coupled to the elongate members 462, 472 as shown in FIGS. 13 and 14.

A first link 510 of the multi-bar linkage 508 is pivotally coupled to the elongate member 462 adjacent the proximal end 464 of the instrument 460. An opposite end of the link 510 from the elongate member 462 is captured via a pin 512 within a slot 514 of an actuating link 516. A distal end of the actuating link 516 is pivotally coupled via a pin 518 to the second elongate member 472 as shown in FIGS. 13-14. The second elongate member 472 slides relative to the first elongate member 462 as a result of the manipulation of the linkage 508. As the actuating link 516 is rotated towards the elongate member 462, the link 510 pivots upwardly thereby pulling the actuating link 516 and an associated sliding link 520 upwardly and closing and pulling the jaw 504 closer to the recess 500 at the distal end 466 of the elongate member 462 and clamping the connecting element 16 therein. A locking mechanism 522 in the form of a rotatable knob may be provided on the sliding link 520 to secure the sliding link 520 relative to the elongate member 462 and lock the clamped connecting element 16 in place during manipulation and insertion of the connecting element 16 to the spinal fixation construct 10. The position of the jaw 504 relative to the distal end 466 of the elongate member 462 may be adjusted by moving the pin 512 of the link 510 within the slot 514 provided in the actuating link 516 to accommodate different sized connecting elements 16 and thereby adjust the relative position of the sliding link 520 relative to the elongate member 462 during the clamping operation.

Figure 16:
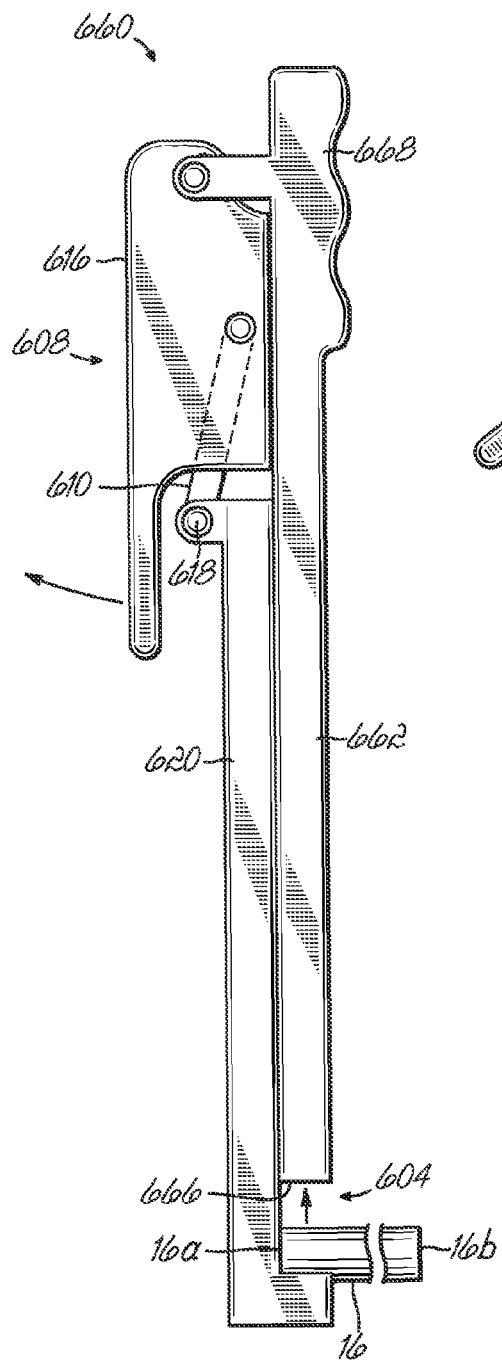
FIG. 16 is a side elevational view of an installation tool according to a sixth embodiment of this invention adapted to manipulate a spine rod into vertebral anchors inserted in respective vertebrae.
Figure 17:
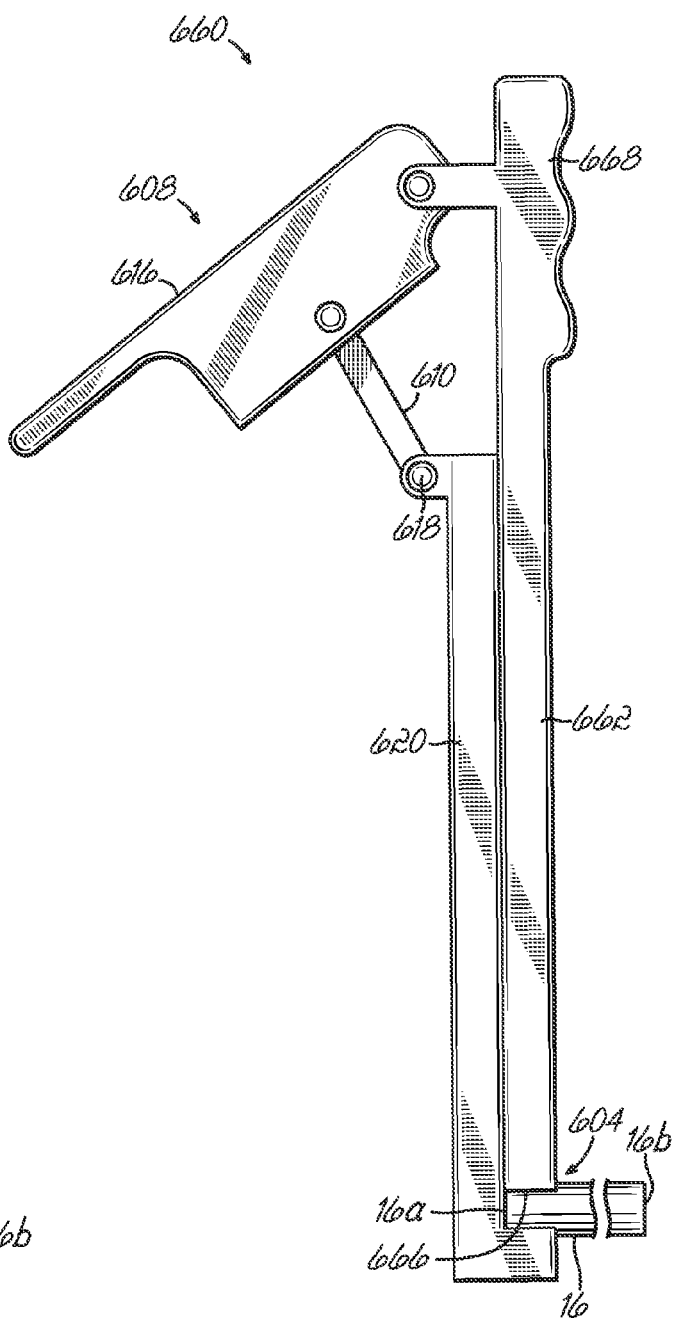
FIG. 17 is a view similar to FIG. 16 with the installation tool engaged with the spine rod.

Another embodiment of an installation tool 660 according to this invention is shown in FIGS. 16-17. This embodiment is similar to the embodiment shown in FIGS. 13-15 wherein a multi-bar linkage assembly 608 is utilized in combination with the elongate member 662 to selectively clamp the connecting element 16 with the jaw 604 and the distal end of the elongate member 666. However, one difference between the embodiment of FIG. 16-17 relative to the embodiment of FIGS. 13-14 is that the actuating link 616 is pivotally coupled directly to the elongate member 662 with the link 610 coupled to the actuating link 616 and the sliding link 620. The clamp 660 is actuated by rotation of the actuating link 616 away from the elongate member 662 as shown in FIG. 16. The more collapsed orientation of the linkage assembly 608 provides for more efficient insertion of the instrument 660 through the incision 18. The clamped orientation of the tool 660 shown in FIG. 17 provides for manipulation and insertion of the connecting element 16 relative to the vertebral anchor head channels 30 as previously described.

Figure 18:
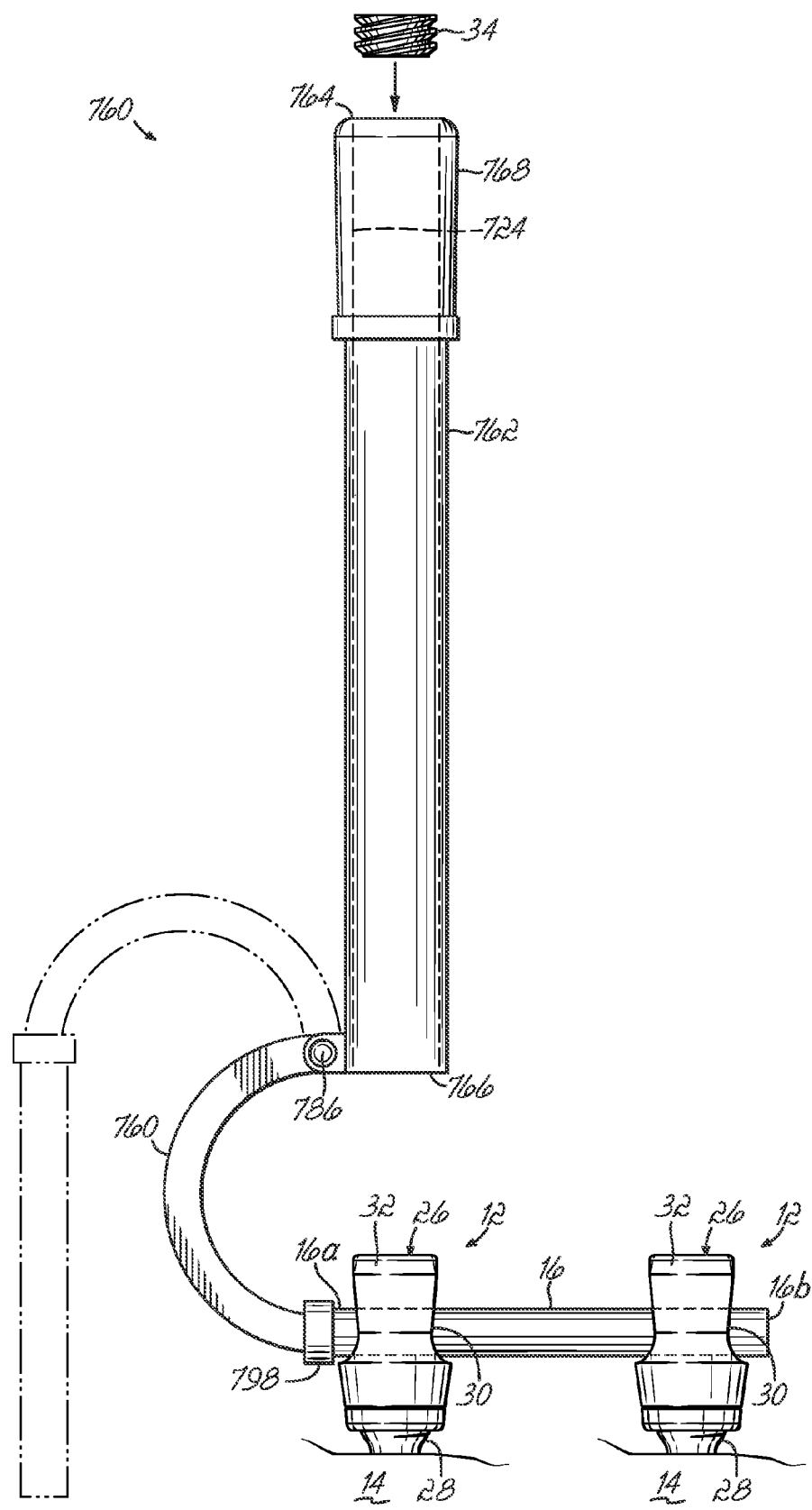
FIG. 18 is a side elevational view of an installation tool according to a seventh embodiment of this invention adapted to manipulate a spine rod into vertebral anchors inserted in respective vertebrae.

Another embodiment of a tool 760 according to this invention is shown in FIG. 18 in which the elongate member 762 includes a lumen 724 extending there through and a handle 768 mounted on the proximal end 764 of the elongate member 762. The connecting element retainer 770 is pivotally mounted to the distal end 766 of the elongate member 762 via a pivot mechanism 786 joining an arcuate-shaped retainer 770 to the elongate member 762. A rod capture device in the form of a collar 798 is provided on an end of the arcuate member 770 opposite from the pivot mechanism 786 to thereby capture the connection element 16 for insertion into the channels 30 of the vertebral anchor heads 26. The connecting element 16 and installation tool 760 may be inserted through the incision 18 in a generally vertical or parallel orientation as shown in phantom lines of FIG. 18. Once the connecting element 16 is positioned adjacent the vertebral anchor heads 26, the pivoting mechanism 786 rotates the connecting element 16 into a generally perpendicular orientation relative to the lumen 724 and longitudinal axis of the elongate member 762 for insertion into the channels 30 of the vertebral anchor heads 26. Advantageously, the lumen 724 provides access for the set screw 34 to be inserted into the vertebral anchor head 26 for securing the connecting element 16 thereto. The connecting element retainer 770 is then disengaged from the connecting element 16 for removal of the installation tool 760 as previously described.

As a result of the various embodiments of this invention, a more minimally invasive spinal fixation construct installation tool and procedure is provided by the pedicle screw assemblies, sleeves and associated devices of this invention without the need for extended incision and associated difficulties. Moreover, increased visualization and minimally invasive disruption are realized with this invention.

From the above disclosure of the general principles of this invention and the preceding detailed description of at least one embodiment, those skilled in the art will readily comprehend the various modifications to which this invention is susceptible. Therefore, we desire to be limited only by the scope of the following claims and equivalents thereof.

We claim:

1. A tool for manipulating a connecting element into position relative to vertebral anchors as part of a spinal fixation construct being installed onto a patient's spinal column, the tool comprising:
   a first elongate member having a proximal end spaced from a distal end, the distal end being configured for insertion through an incision in a patient for placement proximate to a first vertebral anchor coupled to a vertebra of the spinal column;
   a first handle proximate the proximal end of the first elongate member and configured to be grasped by a surgeon; and
   a connecting element retainer proximate the distal end of the first elongate member, the connecting element retainer having a recess configured to receive and selectively and non-pivotably retain the connecting element therein in a generally perpendicular orientation relative to the first elongate member at the connecting element retainer such that the connecting element is configured for insertion through the incision in an orientation generally perpendicular to the spinal column and subsequent subcutaneous re-orientation generally parallel to the spinal column;
   a second elongate element slidably and non-rotatably coupled to the first elongate element at a medial position between the distal and proximal ends of the first elongate element.

2. The tool of claim 1 further comprising:
   an actuating link proximate a proximal end of the second elongate member and configured to be grasped by a surgeon.

3. The tool of claim 1 wherein the connecting element retainer includes an adjustable jaw to accommodate a range of sizes of the connecting element.

4. The tool of claim 3 further comprising:
   a multi-component linkage coupled to the first elongate element and adapted to actuate the adjustable jaw to clamp the connecting element in the adjustable jaw.

5. The tool of claim 4 wherein the multi-component linkage includes a first link pivotably coupled to a second link.

6. The tool of claim 5 wherein the second link is axially slidable along the first elongate member.

7. A tool kit for manipulating a connecting element into position relative to vertebral anchors as part of a spinal fixation construct being installed onto a patient's spinal column, the tool kit comprising:
   a first elongate member having a proximal end spaced from a distal end having a distally-facing arcuate recess, the distal end being configured for insertion through an incision in a patient for placement proximate to a first vertebral anchor coupled to a vertebra of the spinal column;
   a first handle proximate the proximal end of the first elongate member and configured to be grasped by a surgeon;
   a connecting element retainer proximate the distal end of the first elongate member and configured to selectively and rigidly retain the connecting element in an orientation generally perpendicular to the first elongate member at the connecting element retainer such that the connecting element is not movable relative to the first elongate member for insertion through the incision in an orientation generally perpendicular to the spinal column and subsequent subcutaneous re-orientation generally parallel to the spinal column; and
   an extension member configured to be selectively coupled to one of the vertebral anchors secured to an associated vertebra and to provide percutaneous access to the vertebral anchor when coupled thereto;
   wherein the connecting element retainer includes a second elongate member axially slidable relative to the first elongate member, the second elongate member having a proximally-facing arcuate recess configured to axially move towards the distally-facing arcuate recess to clamp the connecting element therebetween.

8. The tool kit of claim 7 further comprising:
   a primary lumen in the extension member generally aligned coaxially with the vertebral anchor when coupled thereto, the primary lumen providing percutaneous axial access to the vertebral anchor; and
   a recess on the extension member offset from the primary lumen and configured to direct and guide the first elongate member and connecting member coupled thereto percutaneous off-axis access to the vertebral anchor.

9. The tool kit of claim 7 further comprising:
   a deformation arrangement on the extension member permitting a portion of the extension member to deform during installation and removal of the extension member on to and from, respectively, the vertebral anchor.

10. The tool kit of claim 7 wherein the vertebral anchor is a pedicle screw having a threaded shaft adapted to be inserted into a pedicle of the vertebra and an anchor head adapted to be positioned in a plurality of orientations relative to a longitudinal axis of the threaded shaft.

11. The tool kit of claim 10 further comprising:
   a set screw adapted to pass through the primary lumen and threadably engage the anchor head and secure the connecting member relative to the vertebral anchor.

* * * * *